US00PP24545P3

(12) United States Plant Patent
Egger

(10) Patent No.: US PP24,545 P3
(45) Date of Patent: Jun. 10, 2014

(54) ***HEUCHERA* PLANT NAMED 'GINGER SNAP'**

(50) Latin Name: ***Heuchera* sp.**
Varietal Denomination: Ginger Snap

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 141 days.

(21) Appl. No.: 13/507,934

(22) Filed: Aug. 7, 2012

(65) Prior Publication Data

US 2014/0047602 P1 Feb. 13, 2014

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by small, heavily veiled, lightly ruffled leaves that are red brown in spring, winter leaves olive green with a white veil, very short flowering stems of pink flowers, reblooming all spring, summer, and fall, small, multi-crowned, low mounding habit, and good vigor.

1 Drawing Sheet

Botanical denomination: *Heuchera* sp.
Variety designation: 'Ginger Snap'.

BACKGROUND OF THE INVENTION

The present invention relates to a new and distinct cultivar of *Heuchera* and given the cultivar name of 'Ginger Snap'. *Heuchera* is in the family Saxifragaceae. *Heuchera* 'Ginger Snap' is the end product of a planned breeding program to create miniature *Heuchera* for small pots. This new cultivar originated from a cross between *Heuchera* K420-2, a proprietary non-commercial hybrid, as the seed parent, and *Heuchera* K360-1, a proprietary non-commercial hybrid, as, as the pollen parent.

Compared to the seed parent, *Heuchera* K420-2, the new cultivar has leaves that are well veiled and lightly ruffled and red brown rather than very lightly veiled, not ruffled, and dark.

Compared to the pollen parent, *Heuchera* K360-1, the new cultivar is similar with a better crown and flowering habit.

Compared to *Heuchera* 'Milan', U.S. Plant Pat. No. 21,682, the new cultivar is smaller overall with lighter pink flowers and main leaf color red brown to olive green rather than silver purple to silver.

Compared to *Heuchera* 'Vienna', U.S. Plant Pat. No. 23,308, the new cultivar has a smaller habit and smaller, more ruffled leaves that have red brown rather than orange in the background color.

This new *Heuchera* is uniquely distinguished by:

1. small, heavily veiled, lightly ruffled leaves that are red brown in spring,
2. winter leaves olive green with a white veil,
3. very short flowering stems of pink flowers,
4. reblooming all spring, summer, and fall,
5. small, multi-crowned, low mounding habit, and
6. good vigor.

This new cultivar has been reproduced only by asexual propagation (tip cuttings and tissue culture). Each of the progeny exhibits identical characteristics to the original plant.

Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a two-year-old plant of *Heuchera* 'Ginger Snap' growing in a one gallon pot in a cold greenhouse in April in Canby, Oreg.

FIG. 2 shows a one-year-old plant of *Heuchera* 'Ginger Snap' growing in a one gallon pot in a cold greenhouse in August in Canby, Oreg.

DETAILED PLANT DESCRIPTION

The following is a detailed description of the new *Heuchera* cultivar based on observations of two-year-old specimens growing in one gallon containers in a cold greenhouse in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The *Royal Horticultural Society Colour Chart,* 2007 edition.

Plant:

*Form.*—Basal rosette, herbaceous perennial.
*Hardiness.*—USDA Zone 4 to 9.
*Size.*—12 cm tall from top of the foliage to the ground and 25 cm wide.
*Habit.*—Mounding.
*Vigor.*—Good.

Leaf:

*Type*.—Simple.

*Arrangement*.—Rosette.

*Number*.—About 40.

*Shape*.—Broadly ovate to orbicular.

*Lobing/division*.—5 to 7 lobes.

*Venation*.—Palmate.

*Margins*.—Crenate and lightly undulate.

*Apex*.—Mucronulate.

*Base*.—Cordate and overlapping.

*Blade size*.—Grows to 6.5 cm long and 6.5 cm wide.

*Surface texture*.—Glandular on top and bottom.

*Petiole description*.—Grows to 8.5 cm long and 1.5 mm wide, glandular hairs, Greyed Purple 187C.

*Leaf color*.—Color variable, topside spring, summer and fall, new leaves Greyed White NN155A over a background of Greyed Red 181A with the veins Greyed Red 181A, background color on mature leaves changes to Greyed Orange 165A and later in winter to Yellow Green 148A; bottom side all seasons Greyed Purple 187B.

Inflorescence:

*Size*.—Grows to 3.5 cm wide and 6 cm long.

*Type*.—Thyrse.

*Number of flowers per thyrse*.—About 30.

*Number of thyrse*.—About 10 in the first spring flush, reblooming all summer.

*Peduncle*.—Grows to 11.5 cm long, 1 mm wide at base, Greyed Purple 187B, glandular hairs.

*Pedicel*.—Variable in size, with glandular hairs, Greyed Purple 187B.

*Bloom period*.—April through October in Canby, Oreg.

Flower bud:

*Size*.—2.5 mm wide and 4 mm long.

*Description*.—Glandular puberulent, ovoid, down facing.

*Color*.—Red 48C.

Flower:

*Type*.—Perfect.

*Shape*.—Campanulate.

*Size*.—6 mm long and 5 mm wide.

*Corolla description*.—5 petals, 3 mm long and 0.5 mm wide, reflexed, narrowly spatulate, margins entire, tip acute, glabrous top and glandular on bottom, White N155B.

*Calyx description*.—Campanulate, 5 mm long and 5 mm wide, with 5 lobes divided ½ way to the base, each 1.5 mm wide and 2 mm long, glandular hairs outside and glabrous inside, tips obtuse, margin entire; color both sides Red Purple 62B.

*Stamen description*.—5 in number, filaments 3.5 mm long, White NN155C, anthers 0.2 mm, Red 37A, pollen Orange 26A.

*Pistil description*.—1, 2-beaked, 4 mm long and 1.5 mm wide; Yellow Green 145C overall, ovary 1.5 mm long and 1.5 mm wide; style 2.5 mm long.

*Fragrance*.—None.

*Lastingness*.—Each thyrse blooms for about 3 weeks on the plant.

Fruit and seed: None seen.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

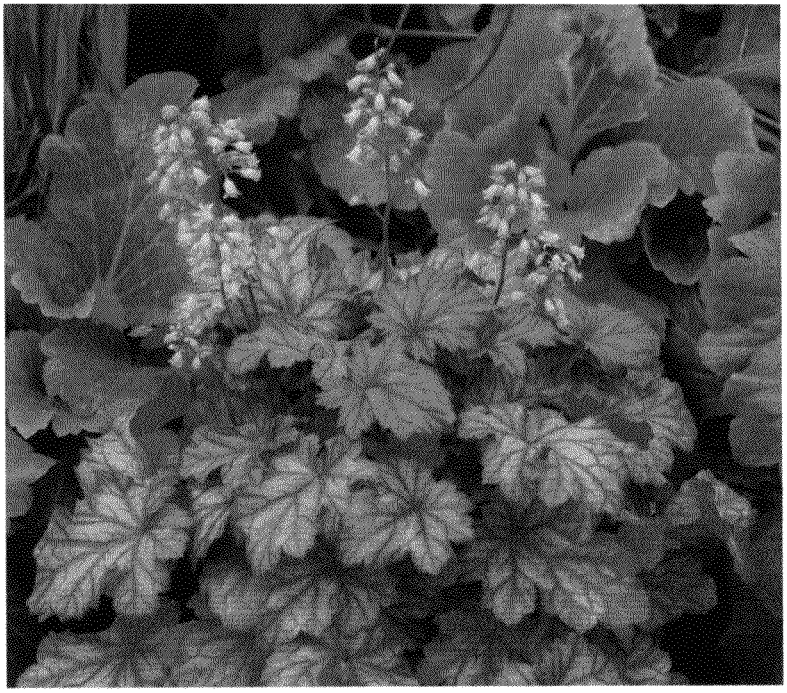

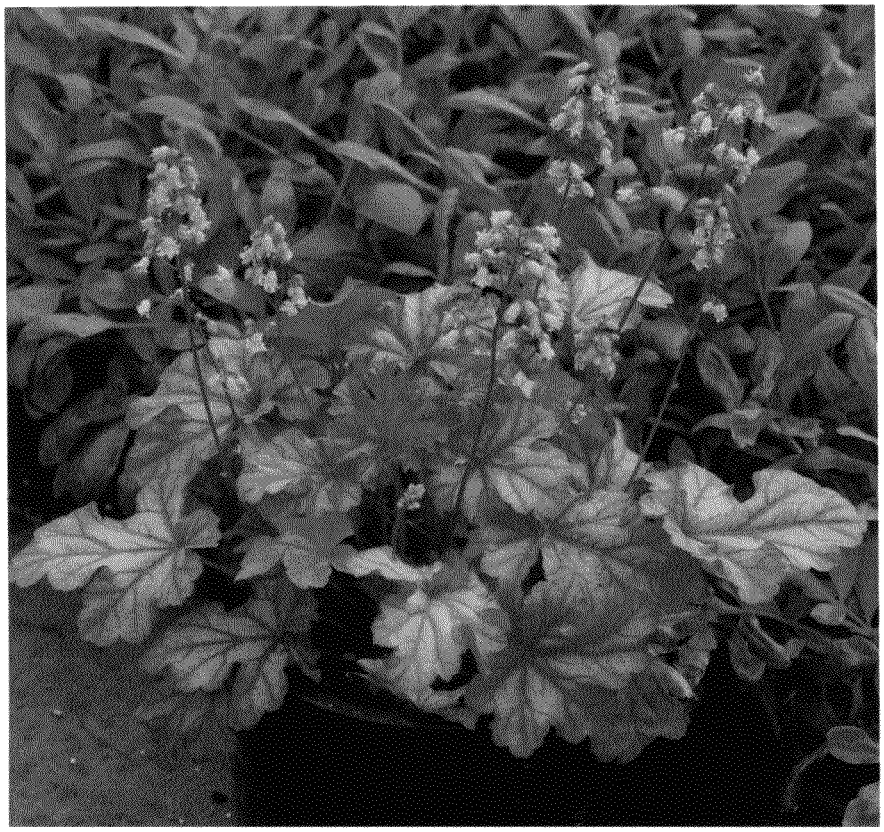
FIG. 1 above, FIG. 2 below